United States Patent [19]

Danzger

[11] Patent Number: 5,503,620
[45] Date of Patent: Apr. 2, 1996

[54] BACK SUPPORT BELT APPARATUS AND METHOD

[75] Inventor: Joshua Danzger, Brooklyn, N.Y.

[73] Assignee: Charm-Tex Inc., Brooklyn, N.Y.

[21] Appl. No.: 269,527

[22] Filed: Jul. 1, 1994

[51] Int. Cl.⁶ ........................................................ A61F 5/00
[52] U.S. Cl. .................... 602/19; 128/100.1; 128/101.1; 128/876; 2/310; 2/311; 2/321
[58] Field of Search .................................. 602/5, 19, 75; 2/44, 338, 310, 311, 322, 321; 128/101.1, 100.1, 876

[56] References Cited

U.S. PATENT DOCUMENTS

| | | | |
|---|---|---|---|
| 3,613,679 | 10/1971 | Bijou | 602/75 |
| 4,137,759 | 2/1979 | Talbert | 73/143 |
| 5,111,806 | 5/1992 | Travis | 602/19 |
| 5,334,134 | 8/1994 | Saunders | 602/19 |
| 5,349,706 | 9/1994 | Keer | 2/300 |
| 5,387,183 | 2/1995 | Jones | 602/19 |
| 5,399,151 | 3/1995 | Smith | 602/19 |

*Primary Examiner*—Richard J. Apley
*Assistant Examiner*—Kim M. Lee
*Attorney, Agent, or Firm*—James J. Romano, Jr.

[57] ABSTRACT

A back support belt comprising a primary support belt including fasteners for fastening the same generally at the frontal area of the waist of the wearer, and a secondary tensioning belt comprising fasteners for fastening the same around the primary support belt generally at the frontal area of the waist of the wearer is provided, and includes back support belt color tensioning indicators on the secondary tensioning belt which are visible only from the rear and side areas of the waist of the wearer, and thus not by the wearer, and which are operable to indicate both when the back support belt is properly tensioned around the waist of the wearer, and when the back support belt is not properly tensioned around the waist of the wearer. The back support belt color tensioning indicators are operable to indicate proper and improper tensioning of the support belt independently of the relationship between the size of the support belt and the waist size of the wearer to thus be virtually foolproof in operation. For use in instances wherein the wearer of the back support belt is forced to work in the absence of anyone qualified to observe the color tensioning indicators on the secondary tensioning belt, the back support belt will further include an additional color tensioning indicator taking the form of non-obscurable alignment marks formed on one of the primary support belt fasteners and co-operable with one of the secondary tensioning belt fasteners to indicate proper back support belt tensioning. The additional color tensioning indicator is not, however, operable independently of the relationship between the size of the support belt and the waist size of the wearer, and are thus not foolproof in operation.

18 Claims, 5 Drawing Sheets

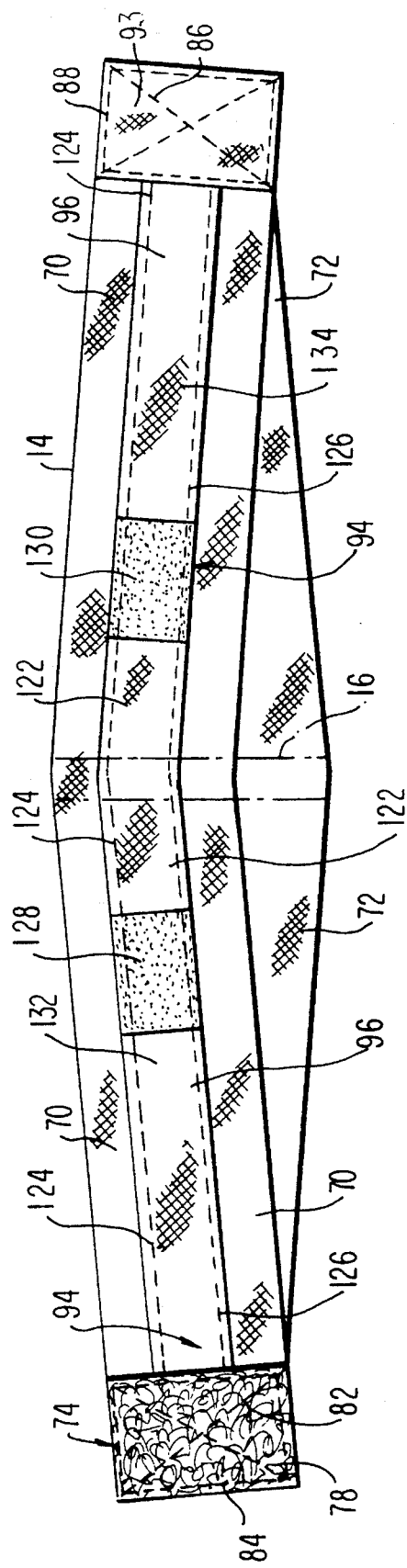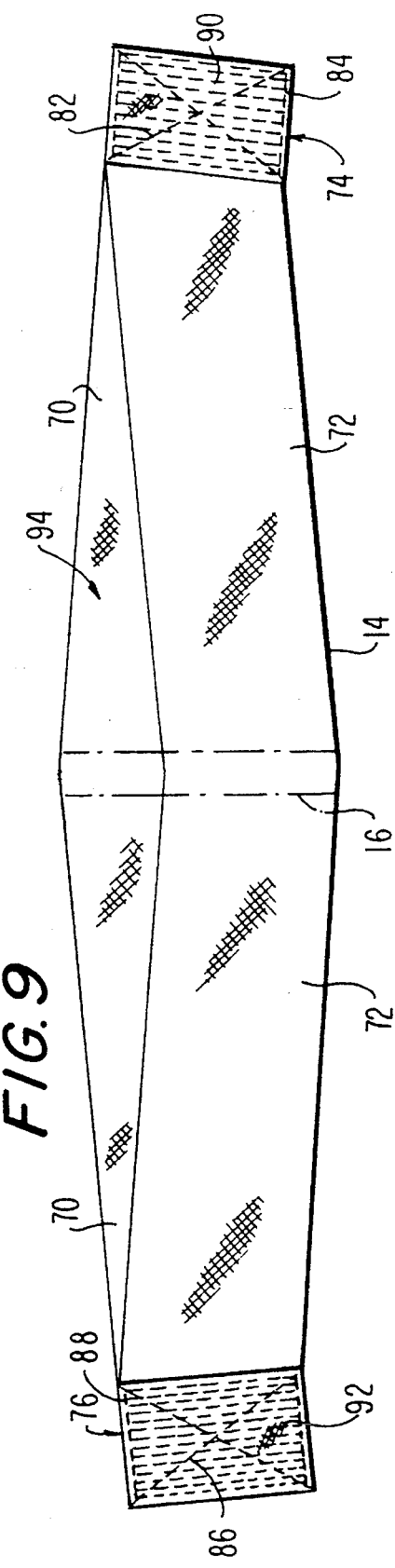

BACK SUPPORT BELT APPARATUS AND METHOD

BACKGROUND OF THE INVENTION

1. Field of the Invention

This invention relates to new and improved back support apparatus and method for use by workpersons or athletes or the like routinely involved in heavy lifting; and, more particularly, to an elastic back support belt and method of operation thereof which are effective to provide increased support for abdominal muscles and back muscles in the lumbar region with readily observable, virtually foolproof indicator of the correct utilization of the support belt by the wearer to insure that such increased back support is, in fact, being properly provided to the wearer by the support belt.

2. Description of the Prior Art

Although back support belts for workpersons or athletes or the like routinely involved in heavy lifting are generally well known in the prior art, none are known which include readily observable, virtually foolproof indicator of the correct utilization of the support belt by the wearer.

More specifically, U.S. Pat. No. 5,111,806 to Travis discloses a Support Belt With Color Indicator which includes a color indicator to indicate proper tensioning of the belt around the midsection of the wearer, and thus proper support of the wearer's abdominal and back muscles. In Travis, however, the color indictor is located at the front of the support belt in the area generally occupied by the buckle of a conventional belt to thereby render the color indicator readily obscurable when the wearer of the belt is bending over to pick up a load, or carrying the same from one place to another, and thus very difficult if not impossible to observe by a supervisor or workplace safety inspector to insure that the support belt is properly tensioned. In addition, the color indicator of Travis is by no means fully reliable in that the desired condition, namely the complete covering of the color indicator at the front of the support belt by a secondary belt fastening portion to indicate that the belt is properly tensioned, could be arrived at by the wearer inadvertently utilizing an oversized support belt; in which instance the belt would not be providing proper support for the back of the wearer despite the covering of the color indicator as above to indicate that it was.

U.S. Pat. No. 5,070,866 to Alexander et al discloses a Woven Back Support Belt With Rigidity Control which utilizes a hinging action within the belt webbing to increase the rigidity of the support belt. Although the use of different colors for different belt plies is disclosed by Alexander et al, this is for esthetic reasons, only, and has no relevance of any nature to proper support belt tensioning.

U.S. Pat. No. 4,841,961 to Burlage et al discloses a Patient Restraining Device and Temporary Transport which operates to secure a patient to a transport apparatus in the nature of a backboard or gurney. Color coding can be employed in this device, but is only effective to insure that the device is applied "right side up" to the patient, and again has no relevance of any nature to proper tensioning of the device which is, in any event, not directed to patient back support.

U.S. Pat. No. 3,920,008 to Lehman discloses a Support Belt particularly adapted to routine wear by surgical patients who have had operations affecting the abdominal area and which includes primary and secondary bands for fastening around the waist of the wearer to provide abdominal support, but is totally lacking in the disclosure of any color indicator to insure proper tensioning of the belt.

In summary, it is thus to be understood that no prior art is known which discloses or makes obvious the elastic back support belt or method of belt operation of my invention.

OBJECTS OF THE INVENTION

It is, accordingly, an object of my invention to provide new and improved back support belt apparatus and method of operation thereof for use by workpersons or athletes or the like routinely involved in heavy lifting to provide increased support for abdominal muscles and back muscles in the lumbar region, thereby operating to assist in preventing back injuries.

It is another object of my invention to provide support belt apparatus and method of operation as above which include generally non-obscurable readily observable color indicator to indicate proper tensioning of the belt around the lower back of the wearer and attendant proper support by the belt for the lower back of the wearer.

It is another object of my invention to provide support belt apparatus and method of operation thereof which include virtually foolproof color indicator to indicate proper tensioning of the belt around the lower back of the wearer and attendant proper support by the belt for the lower back of the wearer.

It is another object of my invention to provide support belt apparatus and method of operation thereof which are readily and conveniently utilizable, and consistent in all material respects with known manners of back support belt utilization, and which thus require no specialized training or the like for the proper and effective employment thereof.

It is a further object of my invention to provide support belt apparatus as above which are of generally straightforward construction, and which require the use of only readily available materials of proven dependability and like manufacturing techniques in the fabrication thereof to thus provide for relatively low support belt manufacturing costs, and long periods of satisfactory useful support belt life.

It is a still further object of my invention to provide support belt apparatus and method of operation thereof as above which require observation of the color indicator by a person other than the wearer to verify proper tensioning of the belt apparatus around the wearer's lower back, thus preventing purposeful, as through simple laziness or inattention, or simply inadvertent, improper tensioning of the support belt apparatus by the wearer with attendant improper support for the lower back of the wearer by the support belt apparatus.

It is a still further object of my invention to provide support belt apparatus and method of operation as above which include non-obscurable alignment marks visible at the front portion thereof in addition to the color indicator means to indicate proper support belt tensioning within reasonable tolerances and enable the determination of the same by the wearer of the belt alone in those instances wherein he or she as the case may be is, of necessity, unaccompanied by other persons qualified to observe the color indicator means in the performance of his or her lifting tasks.

SUMMARY OF THE INVENTION

As disclosed herein, the new and improved back support belt apparatus and method of my invention take the form of a primary support belt including fastening means to fasten the same generally around the waist of the wearer, and a secondary tensioning belt including fastening means to fasten the same around the primary support belt generally around the waist of the wearer to tension the back support belt. Both the primary support belt and secondary tensioning belt fastening means are operable to fasten the same generally at the frontal area of the waist of the wearer. The secondary tensioning belt includes back support belt tensioning indicator means which are disposed thereon remote from the belt fastening means generally to the rear area of the waist of the wearer so as to be readily visible therefrom except to the wearer of the support belt; and take the form of a pair of spaced "danger" colored strips which are only visible when the back support belt is not properly tensioned to thus clearly indicate that the back support belt is not providing proper support for the abdominal and lower back muscles of the wearer, and a pair of spaced "safe" colored elastic strips which are only visible when the back support belt is properly tensioned and thus providing proper support for the abdominal and lower back muscles of the wearer. The back support belt is particularly adapted for use by workpersons or athletes or the like routinely involved in heavy lifting; with the disposition of the back support belt tensioning indicator means remote from the belt fastening means rendering the former virtually foolproof in operation, for example fully effective to immediately indicate the wearing of an oversized back support belt, and the disposition of the tensioning indicator means generally at the rear area of the waist of the wearer insuring the immediate visibility thereof even when the wearer is bent over a load or carrying the same.

For use in instances wherein the wearer of the belt is, by necessity, forced to work alone and thus unaccompanied by anyone who can observe the tensioning indicator means to insure proper support belt tensioning, the back support belt apparatus and method of my invention will further comprise non-obscurable alignment marks at the front portion of the support belt so as to be visible by the wearer and operable to indicate proper belt tensioning within reasonable tolerances and strictly dependent upon proper sizing of the support belt to waist of the wearer.

DESCRIPTION OF THE DRAWINGS

The above and other significant objects and advantages of the support belt apparatus and method of operation thereof of my invention are believed made clear by the following detailed description thereof taken in conjunction with the accompanying detailed drawings wherein;

FIG. 8 is a plan view of the secondary tensioning belt of the support belt apparatus of FIG. 1 as removed therefrom and seen from the back, with the tunnel members removed for purposes of clearer illustration of the support belt apparatus of the invention;

FIG. 9 is a plan view of the tensioning belt of FIG. 8 as seen from the front;

DETAILED DESCRIPTION OF THE INVENTION

Figure 1:
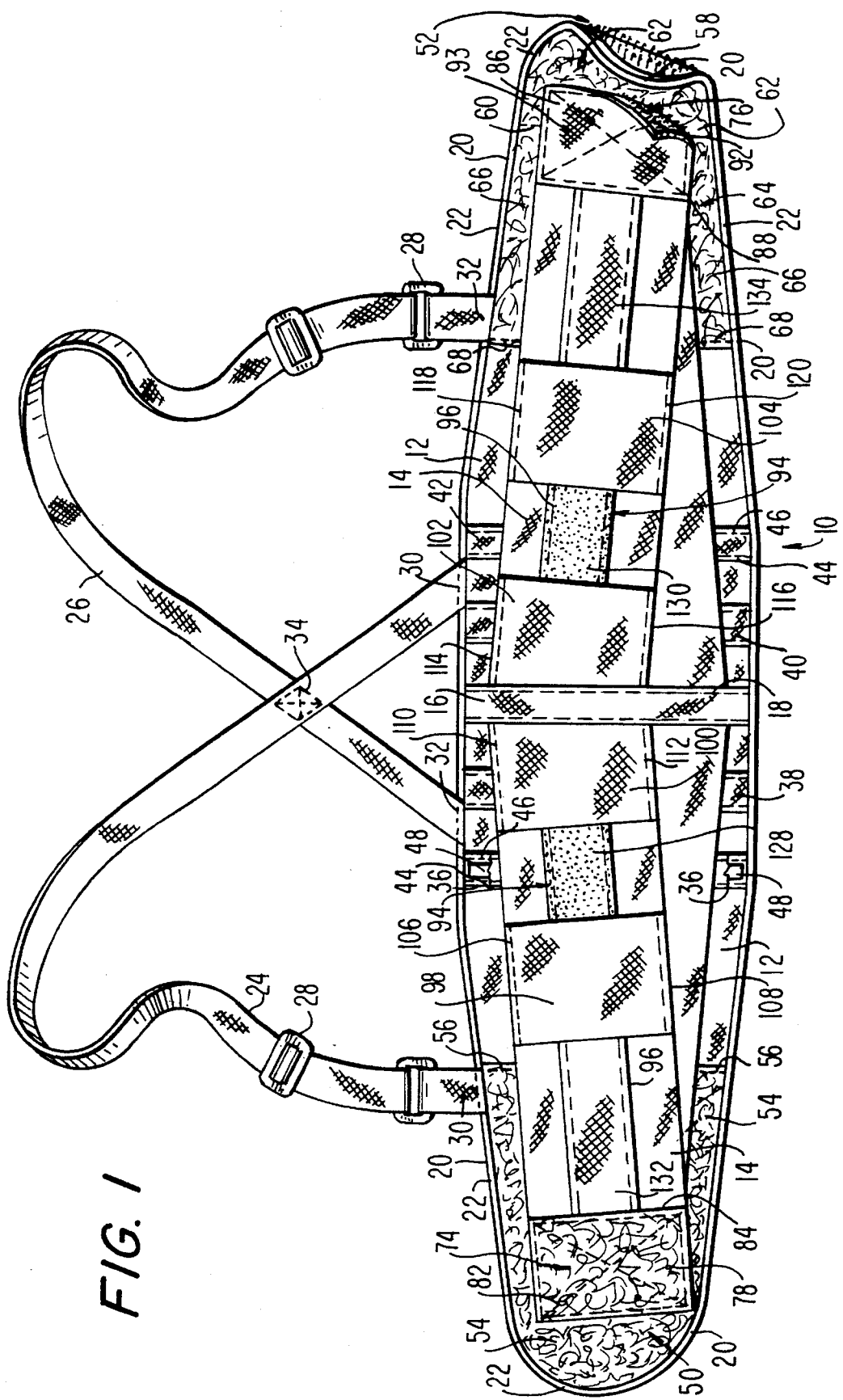
FIG. 1 is a plain view of support belt apparatus configured and operable in accordance with the currently contemplated best mode of my invention, and seen from the back with the belt apparatus laid out essentially flat.
Figure 2:
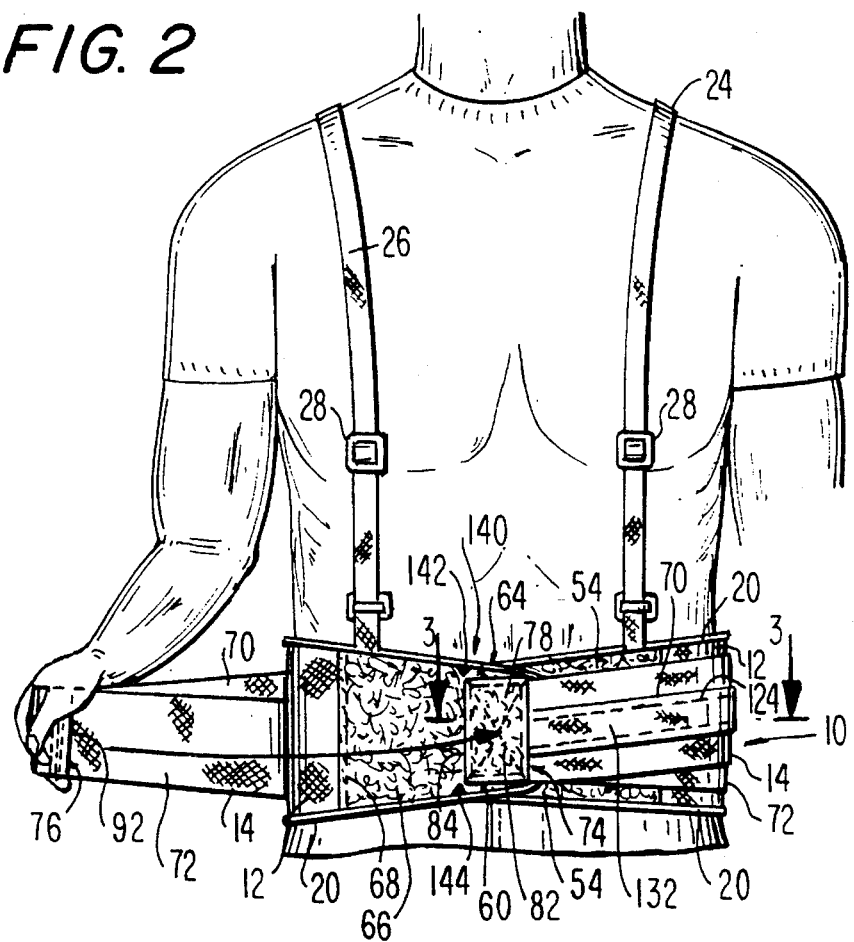
FIG. 2 is a perspective view of the support belt apparatus of FIG. 1 illustrating how the support belt apparatus are fitted around the waist of the wearer as seen from the front, with the belt apparatus partially fastened and untensioned.
Figure 3:
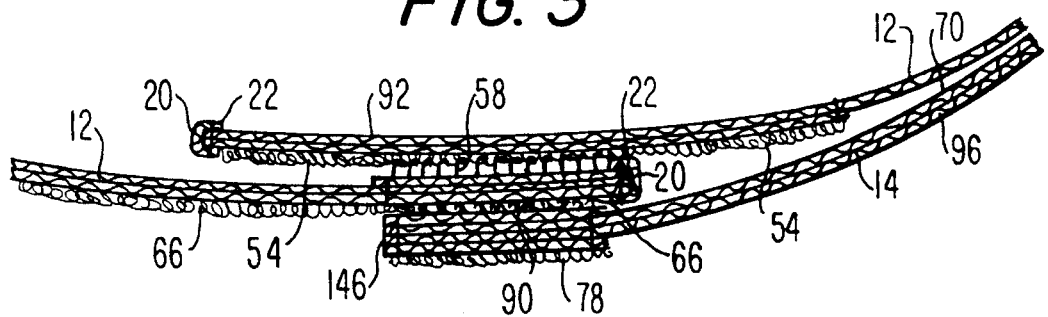
FIG. 3 is a fragmentary cross-sectional view taken essentially along lines 3—3 in FIG. 2.

Referring now to FIGS. 1 and 2 of the application drawings, a back support belt configured and operable in accordance with the currently contemplated best mode of my invention is indicated generally at 10, and comprises a primary support belt as indicated at 12, and secondary tensioning belt as indicated at 14 which overlies the primary support belt 12 as shown and is of lesser width and longitudinal extent than the primary support belt.

The respective primary support belt 12 and secondary tensioning belt 14 are very securely joined together as shown at the generally central positions thereof by aligned reinforcement pieces which lie to either side of the central belt portions, only one of which is shown as indicated at 16, and which are joined together by stitching 18 extending through both of the reinforcement pieces and the respective support and tensioning belt portions which underlie the same.

The primary support belt 12 includes a banding 20 extending around the periphery thereof and secured thereto by stitching as partially illustrated at 22; and suspenders as indicated at 24 and 26, including adjustment buckles 28, are secured as shown to the upper periphery of the primary support belt 12 by stitching as indicated at 30 and 32, respectively. The suspenders 24 and 26 are joined together in conventional manner above the generally central portion of the back support belt 10 as shown by cross stitching as indicated at 34.

The respective primary support belt 12, secondary tensioning belt 14 and suspenders 24 and 26 are made from any readily available elastic fabric material of proven durability and particularly high strength characteristics, for example, spandex.

In use as described in greater detail hereinbelow, the back support belt 10 of my invention is emplaced around the waist of the wearer through use in part of the suspenders 24 and 26 as partially illustrated by FIG. 2, and securely fastened and properly tensioned therearound to provide increased support for, the wearer's abdominal muscles and back muscles in the lumbar region and assist in preventing back injuries attendant heavy lifting by the wearer as described in some detail in U.S. Pat. No. 5,111,806 to Travis and U.S. Pat. No. 5,070,866 to Alexander et al, the respective disclosures of which are hereby incorporated by reference in this specification in that regard.

Referring again in detail to the primary support belt 12, the same will be seen to include back support means taking the form of spaced pairs of generally vertically extending stay support pockets as indicated at 36 and 38, and 40 and 42, which are vertically coextensive as shown with the primary support belt and which are securely stitched thereinto to either side of the central reinforcement and joinder belt piece 16 by stitching as indicated at 44 and 46, respectively. A generally elongated stay member as illustrated at 48 for stay support pocket 36, only, is secured in each of the stay support pockets 36, 38, 40 and 42 to extend generally coextensively thereof between the top and bottom edges of the primary support belt 12. These stays are made from any readily available relatively stiff resilient material, for example spring steel, and are effective to support the abdominal and back muscles of the wearer of the back support belt and resist curvature of the wearer's spine attendant heavy lifting.

Further included in the primary support belt 12 are belt fastening means as indicated generally at 50 and 52 and disposed as shown on opposite end portions of the primary support belt 12 to very securely fasten the same together and thus secure the primary support belt 12 around the waist of the wearer. More specifically, and as best seen in FIGS. 1 and 2 of the application drawings, the fastening means 50 comprise a generally U-shaped pad 54 of loop material, for example Velcro, which overlies the material of the primary support belt 12 at the left end portion thereof as seen in FIG. 1, and the respective outer edges of which underlie the banding 20 and are thus securely attached to the primary support belt 12 by the stitching 22 which attaches the banding 20 to the belt 12, and by the stitching 30 which attaches the suspender 24 thereto. An additional line of stitching 56 at the inner end portion of the pad 52 to the primary support belt 12 completes the particularly secure attachment of the pad 52 to the primary support belt 12. The fastening means 52 comprise a generally U-shaped pad 58 of hook material, again for example Velcro, which underlies the material of the primary support belt 12 at the right end portion thereof as made clear by the folded over right end portion of the belt 12 as illustrated in FIG. 1. The respective outer edges of the pad 58 again underlie the banding 20 for secure attachment thereof to the primary support belt 12 by the stitching 22; while additional lines of vertical and cross stitching as indicated at 60 and 62 in FIG. 2 complete the particularly secure attachment of the hook material pad 58 to the primary support belt 12.

Additional fastening means on the primary support belt 12 are indicated generally at 64 in FIGS. 1 and 2, and comprise a generally U-shaped pad 66 of loop material, again for example Velcro, which is essentially a mirror image of pad 54, and which overlies the material of the primary support belt 12 at the right end portion thereof as seen in FIG. 1, and the respective outer edges of which again underlie the banding 20 and are thus securely attached to the primary support belt 12 by the stitching 22 which attaches the banding 20 to the belt 12, and by the stitching 32 which attaches the suspender 26 thereto. An additional line of stitching 68 completes the particularly secure attachment of the pad 66 to the primary support belt 12.

Referring now in detail to the tensioning belt 14 as best seen in application drawing FIGS. 1, 8 and 9, the same comprises an elastic, upper tensioning belt portion 70 and an elastic, lower tensioning belt portion 72 which extend as shown at a slight angle to each other, with upper tensioning belt portion 70 overlying lower tensioning belt portion 72 in part as made clear by FIGS. 1, 8 and 9. The tensioning belt portions 70 and 72 are very securely attached to each other, and to the primary support belt 12, at the respective generally central areas thereof at the belt reinforcement piece 16 by the stitching 18 which may be understood to extend through all of the same; with the primary function of the tensioning belt 14 being to cooperate with and properly tension the primary support belt 12 to insure the provision of an appropriate lifting force on the wearer's abdominal and back muscles attendant the bending over and heavy lifting by the wearer.

Further included in the tensioning belt 14 at the overlying left ends of the tensioning belt portions 70 and 72 as seen in FIG. 8 are fastening means as generally indicated at 74 which take the form of a generally rectangularly shaped pad 78 of loop material, again for example Velcro, which is very securely attached to those tensioning belt ends to overlie the same as best seen in application drawings 1 and 8 by cross and box stitching as indicated at 82 and 84.

The tensioning belt fastening means 74 further include a like sized and shaped pad of hook material, again for example Velcro, as indicated at 90 which underlies the pad 78 on the underside of the overlying ends of the tensioning belt portions 70 and 72 as best seen in application drawing FIG. 9, and which is also very securely attached to those tensioning belt ends and the paid 78 by the stitching 82 and 84.

Also included in the tensioning belt 14 at the overlying left ends of the tensioning belt portions 70 and 72 as seen in FIG. 9 are fastening means as indicted generally at 76 which take the form of a generally rectangularly shaped pad 92 of hook material, again for example Velcro, which is very securely attached to those tensioning belt ends to underlie the same by cross and box stitching as indicated at 86 and 88. Overlying the pad 92 at the right end of the tensioning belt 14 as seen in FIG. 8 is the folded over end 93 of the lower tension belt portion 72 which is also secured thereto and to the end of upper tensioning belt portion 70 as shown by the stitching 86 and 88.

The tensioning belt 14 of my invention further includes back support belt color tensioning indictor means as indicated generally at 94 in application drawing FIGS. 1 and 8, and which function as described in detail hereinbelow to provide readily visible color indication as to the proper tensioning of the back support belt 10 around the waist and lower back of the wearer. The tensioning belt color indicator means 94 comprise a separate tensioning belt piece taking the form of a color indicator band 96 of material which overlies and is generally coextensive with the tensioning belt portion 70 to extend therewith to either side of the reinforcement piece 16 to underlie the pads 78 and 90, and 92, respectively, at opposite ends of the tensioning belt portion 70; and which is accordingly very securely attached thereto by the stitching 18 at the reinforcement piece 16, and by the stitching 82 and 84, and 86 and 88, at the pads 78 and 90, and 92, respectively. As made clear by the drawings, the band 96 is of substantially lesser width than the tensioning belt portion 70.

Elastic tunnel members are indicted at 98, 100, 102 and 104 in FIG. 1 of the application drawings, and respectively comprise spaced strips of elastic material which overlie the tensioning belt portion 70 and the color indictor band 96.

Tunnel member 98 is securely attached to the upper and lower edges of the tensioning belt portion 70 by stitching as indicated at 106 and 108; tunnel members 100 and 102 which are formed from a single strip which underlies the reinforcement piece 16 are securely attached to the upper and lower edges of the tensioning belt portion 70 and to the reinforcement piece 16 by stitching as indicated at 110, 112, stitching 18, and stitching as indicated at 114 and 116, respectively; while tunnel member 104 is securely attached to the upper and lower edges of tensioning belt portion 70 by stitching as indicated at 118 and 120.

With all of the heretofore described components of the back support belt 10 of my invention colored black, with the probable exception of the stays 48 which are not in any event visible, it may be understood that, as best seen in application drawing FIG. 8 which depicts the tensioning belt 14 with the tunnel members 98, 100, 102 and 104 removed for purposes of clearer illustration of my invention, the color indicator band 96 comprises a central indicator strip 122 extending to either side of the reinforcement piece 16 as shown and colored in a readily visible "safe" color, for example white or green, which is securely attached at opposite ends thereof by stitching 124 and 126 to intermediate band indicator strips 128 and 130 of a readily visible "danger" color, for example blaze fluorescent orange or red, which are in turn securely attached at the respective outer ends thereof as shown, again by stitching 124 and 126, to the respective inner ends of black pull strips 132 and 134.

Although dimensions may of course vary, representative widths in accordance with the currently contemplated best mode of my invention are 1⅞ inches for the tunnel members 98, 100, 102 and 104, 1⅞ inches for the "safe" indicator strips 122 to either side of the reinforcement piece 16, and 1¼ inches for the "danger" indicator strips 128 and 130, respectively.

Figure 4:
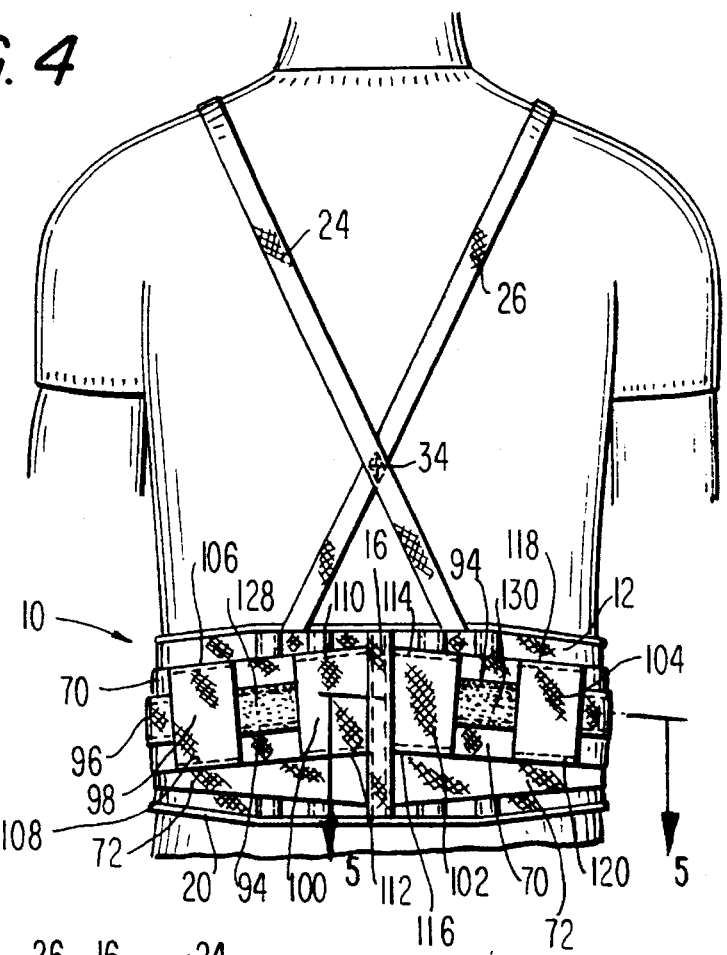
FIG. 4 is a perspective view of the support belt apparatus of FIG. 1 illustrating how the support belt apparatus are fitted around the waist of the wearer as seen from the back, and illustrating the support belt apparatus in the untensioned condition thereof.

For representative use of the back support belt 10 of my invention configured as heretofore described, and properly sized to the waist of the wearer in accordance with the untensioned longitudinal extent of the belt, it may be understood that the arms of the wearer are placed through the openings formed by the suspenders 24 and 26, and the support belt 10 positioned around the waist of the wearer in conventional manner as seen from the front in FIG. 2 and from the back in FIG. 4; with the level of the belt around the waist of the wearer being readily adjustable as may be required by adjustment in the effective lengths of the suspenders 24 and 26 through use of adjustment buckles 28. The primary support belt 12 is then securely fastened around the wearer's waist by the grasping and pulling of the fastening means 50 at the left end portion of the belt as seen in FIG. 1 by the left hand of the wearer, and the grasping and pulling of the fastening means 52 at the right end portion of the belt as seen in FIG. 1 by the right hand of the wearer, thereby stretching the elastic material of the primary support belt 12 to fit snugly yet comfortably around the wearer's waist; whereupon the pad 58 of hook material of fastening means 52 is pressed firmly onto the now underlying pad 54 of loop material of fastening means 50 to securely attach the same together and the primary support belt 12 around the waist of the wearer as clearly illustrated by application drawing FIG. 2.

Figure 5:
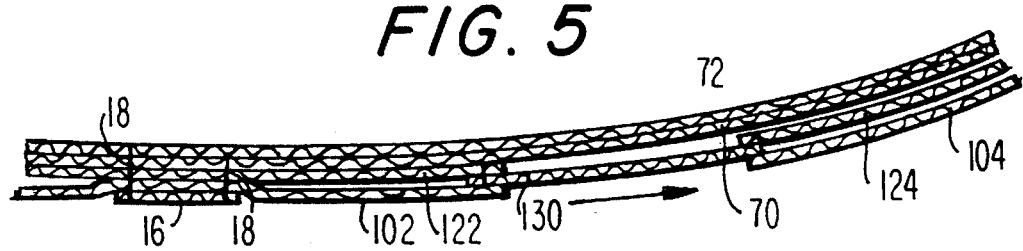
FIG. 5 is a fragmentary cross-sectional view taken essentially along lines 5—5 in FIG. 4.

Fastening of the secondary tensioning belt 14 to in effect seal the closure as above of the primary support belt 12 and insure proper tensioning of the back support belt 10 of my invention around the waist and lower back of the wearer with significantly increased support for the wearer's abdominal muscles then follows, in the presence of a qualified observer, for example a co-worker or supervisor, who stands behind the wearer so as to be able to readily observe the color indicator band 96 of the tensioning belt; and is accomplished by the grasping and pulling of the belt fastening means 74 at the left end of the tensioning belt as seen in FIGS. 1 and 8 by the left hand of the wearer, and the grasping and pulling of the belt fastening means 76 at the right end of the tensioning belt as seen in FIGS. 1 and 8 by the right hand of the wearer. This, of course, operates to stretch the elastic material of the tensioning belt color indicator band 96 relative to the tunnel members 102 and 104, and 98 and 100, respectively, on the tensioning belt portion 70; and is continued under the eye of the observer until the "danger" color indicator strips 130 and 128 have been sufficiently pulled to opposite sides of the tensioning belt portion 70 to be positioned beneath the respective tunnel members 104 and 98 and thus no longer visible between the tunnel members 102, 104 and 100 and 98; and the "safe" color indicator strips 122 have been sufficiently pulled to opposite sides of the tensioning belt portion 70 to be positioned between the tunnel members 102 and 104, and 100 and 98, respectively, and thus readily visible to the eye of the observer to very clearly indicate that the back support belt 10 is now properly tensioned. As this belt condition is reached, the wearer is notified to that effect by the observer, whereupon the pad 90 of hook material of the tensioning belt fastening means 74 in the left hand of the wearer is pressed firmly onto the now underlying pad 66 of loop material of the fastening means 64 of the primary support belt 12 to securely attach the same together as seen in FIG. 2, and the pad 92 of hook material of the tensioning belt fastening means 76 in the right hand of the wearer is pressed firmly onto the now exposed pad of 78 of loop material of the fastening means 74 of the tensioning belt 14 to securely attach the same together at essentially the center of front of the waist of the wearer as indicated by the arrow in application drawing FIG. 2 and illustrated in completely fastened form in application drawing FIG. 5. 10 and 11; thereby completing the proper tensioning of the back support belt 10 to insure that the same is providing proper support to the abdominal and lower back muscles of the wearer.

Figure 6:
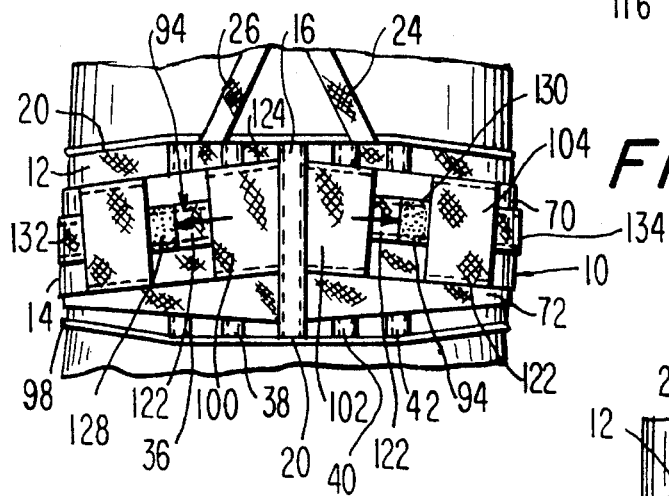
FIG. 6 is a perspective view of the support belt apparatus of FIG. 1 illustrating how the support belt apparatus are fitted around the waist of the wearer as seen form the back, and illustrating the support belt apparatus in the partially, and accordingly, improperly, tensioned condition thereof.
Figure 7:
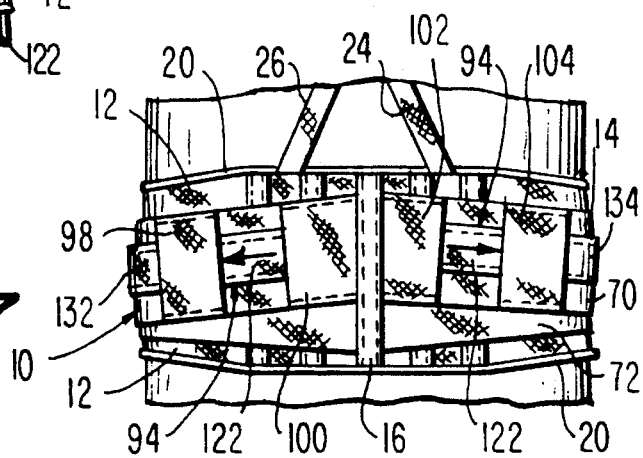
FIG. 7 is a perspective view of the support belt apparatus of FIG. 1 illustrating how the support belt apparatus are fitted around the waist of the wearer as seen from the back, and illustrating the support belt apparatus in the fully, and accordingly properly, tensioned and thus fully effective condition thereof.

With application drawing FIGS. 1 and 4 depicting the support belt 10 of my invention untensioned to thus display only the "danger" colored strips 128 and 130 between the respective tunnel members 98 and 100, and 102 and 104; FIG. 6 depicting the belt only partially, and thus improperly, tensioned to display adjacent, color contrasting portions of the "danger" colored strip 128 and "safe" colored strip 122 between the tunnel members 98 and 100, and adjacent, color contrasting portions of the "danger" colored strip 130 and the "safe" colored strip 122 between tunnel members 102 and 104; and FIG. 7 depicting the belt properly tensioned about the waist and lower back of the wearer to display only the stretched portions of the "safe" colored strip 122 between the respective tunnel members 98 and 100, and 102 and 104; it will be immediately clear to and understood by those skilled in this art that readily observable and virtually foolproof indication of the tensioning of the back support belt 10 of my invention will be provided to any and all qualified observers disposed behind or generally to the side of the wearer by the color tensioning means 94, and this despite the fact that the wearer of the belt may be bent over in the process of lifting up or putting down a load, or simply carrying a load from one place to another to, in either event, obscure the front portion of the back support belt 10 of my invention from the view of any and all qualified observers. Of course, immediately upon observation of improper belt tensioning as above, the wearer of the belt is notified to that effect for immediate corrective action.

In the event that improper tensioning of the back support belt 10 is determined to have been caused by improper fastening of the tensioning belt fastening means 74 and/or 76, the same is simply refastened as above until only the "safe" colored indicator strip 122 is displayed between the respective tunnel members 98 and 100, and 102 and 104, and the wearer of the belt allowed to continue with the tasks at hand. If, on the other hand, proper tensioning of the back support belt 10 simply cannot be achieved despite the best efforts of the wearer at re-fastening the same to that effect, thus making clear that the wearer is preparing for or attempting to work with an oversized back support belt which cannot possibly be properly tensioned about his or her waist, the oversized belt is immediately removed, a properly sized back support belt 10 donned by the wearer and fastened as above to properly tension the same to the satisfaction of the observer, and the wearer again then allowed to commence or continue with the tasks at hand as the case may be.

Certain applications of the support belt apparatus and method of my invention may require that the same be employed by the wearer alone, or in the absence of anyone truly qualified to observe the tensioning indicator means 94 to insure proper tensioning of the support belt apparatus 10 and proper support thereby for the back of the wearer; with one such application occurring, for example, when the wearer of the belt is a local truck driver-delivery man who is forced to work alone without a helper and repeatedly unload and deliver heavy articles thereby requiring repeated bending, and heavy lifting and carrying.

Figure 10:
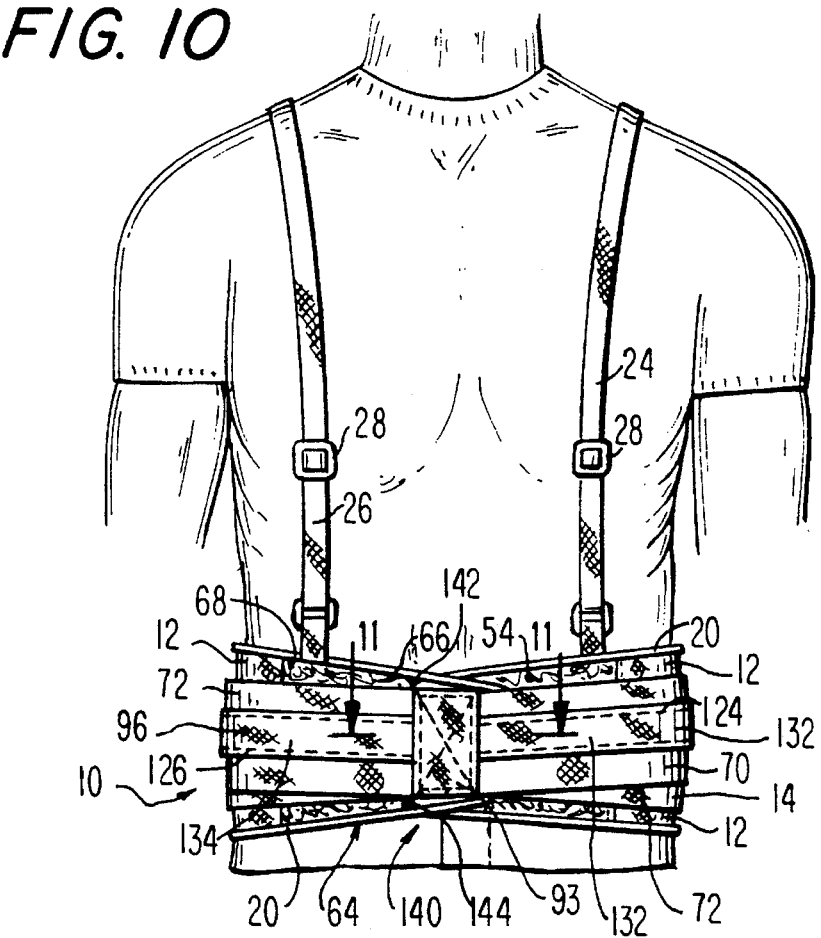
FIG. 10 is a perspective view of the support belt apparatus of FIG. 1 as seen from the front with the apparatus fully fastened and properly tensioned sound the waist of the wearer.
Figure 11:
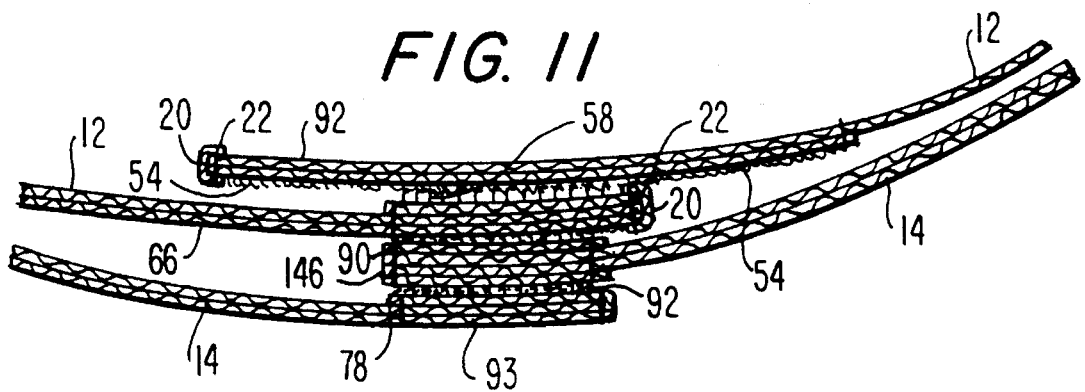
FIG. 11 is a fragmentary cross-sectional view taken essentially along lines 11—11 in FIG. 10 illustrating the overlapping of all relevant support belt apparatus layers.

For such applications, and referring again to application drawing FIGS. 2 and 10, the back support belt apparatus 10 of my invention will be seen to further include additional back support belt tensioning indicator means taking the form of alignment means as generally indicated at 140 and comprising generally wedge shaped alignment marks 142 and 144 disposed as shown on the respective upper and lower edges of the pad 66 of loop material of the primary support belt fastening means 66 immediately inward in each instance of the banding 20. The alignment marks 142 and 144 are colored in a readily and immediately visible color, for example blaze fluorescent orange or red, which contrasts very markedly with the black color of the pad 66, and are formed thereon in any suitable manner, for example by the application of an appropriate dye to the relevant pad portions.

The aligned locations of the alignment marks 142 and 144, which are of course readily visible on the pad 66 by the wearer of the back support belt 10, are carefully predetermined to enable the alignment marks to function as admittedly somewhat limited alternatives, or perhaps supplements as the case may be, to the support belt color tensioning indicator means 94, which are not visible to the wearer of the support belt, in indicating the proper tensioning of the back support belt 10.

More specifically, and with the alignment marks 142 and 144 formed and disposed as described on the pad 66, it may be understood that the unaccompanied wearer of the back support belt 10 is instructed that after emplacing the belt around his or her shoulders and waist and fastening the primary support belt 12 therearound as heretofore described in detail, the pad 90 of loop material which underlies the pad 78 of hook material of the fastening means 74 of the tensioning belt 14 is to be attached as heretofore described to the loop material pad 64 of the primary support belt fastening means 64 in the manner described in FIG. 2 wherein the essentially vertical edge 146 of pads 78 and 90 is in essential alignment with the alignment marks 142 and 144. Thereafter, the further instructions are that the pad 92 of loop material which underlies the folded over tensioning belt portion 93 of the tensioning belt fastening means 76 be attached to the hook material pad 78 of tensioning belt fastening means 74 to completely overlie the same as shown in application drawing FIG. 10 to complete the fastening of the primary back support belt 12 and the secondary tensioning belt 14 around the waist of the wearer.

Of course, the respective aligned locations of the alignment marks 142 and 144 on the primary support belt pad 66 are predetermined in accordance with the waist size of the wearer of the support belt 10 and the corresponding size of the latter to insure proper tensioning of the back support belt 10 of my invention around the waist of the wearer, with the tensioning belt fastening means 74 and 76 fastened to the primary support belt pad 66 and each other as shown and described relative to those alignment marks; in being immediately clear to those skilled in this art that the substantially lesser vertical extent of the aligned and joined tensioning belt fastening means 74 and 76 vis-a-vis the vertical spacing between the alignment marks 142 and 144 renders impossible the covering and obscuring of the alignment marks by those fastening means; whereby the aligned fastening means and alignment marks always remain visible for periodic observation by the wearer of the support belt 10 of my invention to insure that the belt remains properly tensioned about the wearer's waist and lower back.

It will, however, be immediately clear to those skilled in this art that the effectiveness of the alignment marks 142 and 144, per se, in indicating proper tensioning of the support belt 10 is strictly dependent upon the proper sizing of the support belt to the waist of the wearer. This is to say that if, for example, the unaccompanied wearer of the support belt 10 of my invention is incorrectly issued or purchases, as the case may be, an oversized belt, utilization as described in detail hereinabove of the alignment marks 142 and 144 to indicate proper belt tensioning would be totally ineffective to those ends; it being clear that although the edge 146 of pads 78 and 90 of tensioning belt fastening means 74 is aligned with the alignment marks 142 and 144 as depicted in application drawing FIG. 2, and the pad 92 of the tensioning belt fastening means 76 subsequently fastened thereto to completely overlie the same as shown in application drawing FIG. 10 to thereby complete the fastening of the support belt 10 about the waist of the wearer and indicate "proper" belt tensioning, the support belt 10 would not in fact be properly tensioned about the wearer's waist as a result of the incorrect belt sizing relative thereto. Accordingly, extreme care must and will be taken in insuring that a support belt 10 which includes the alignment marks 142 and 144 is properly sized to the waist of the potentially unaccompanied belt wearer before the belt is released to his or her custody as the case may be. Preferably, this can be accomplished in each instance by initially having the potentially unaccompanied wearer of the support belt 10 try the same on in the presence of a qualified observer who can verify through observation of the color tensioning indicator means 94 as described in detail hereinabove that the belt 10 is properly tensioned when the tensioning belt fastening means 74 and 76 are aligned with the alignment marks 142 and 144 as heretofore described.

Although it is generally realized that the problem of on the job back injuries has now become so serious that OSHA is now believed to be considering mandating the use of back support belts of the nature here of interest to prevent back injuries to workers in a wide variety of areas of endeavor wherein relatively heavy lifting is routinely required, ranging from virtually every relevant industrial endeavor, for example, manufacturing and construction, to non-industrial endeavors, for example physical therapists who are routinely required to lift and re-position patients, back injuries are nonetheless still estimated to result in lost wages to workers, and thus lost productivity, in the order of 10 billion dollars per year, a not insignificant portion of which can most probably be directly attributable to improper back support belt design and utilization. Since the back support belt 10 of my invention unquestionably provides a back support belt with readily observable, virtually foolproof means for assuring the proper tensioning thereof, and thus the provision of proper support for the abdominal and lower back muscles of the wearer, at all times during the utilization of the belt, all in full accordance with the stated objects of the invention, there is indeed good reason to believe that the same will contribute materially to significant reduction in lost wages and productivity due to on-the-job back injuries. In addition, and within the strict limitations as set forth in detail hereinabove, it is further believed that the alignment means will provide a particularly useful adjunct to the belt color tensioning indicator means to those ends while extending the range of application of the support belt of my invention to include unaccompanied wearers of the belt.

Various changes may of course be made in the hereindisclosed apparatus and method of my invention without departing from the spirit and scope thereof as defined in the appended claims.

What is claimed is:

1. In a back support belt comprising a primary support belt including fastening means for fastening the primary support belt generally around the waist of the wearer, and a secondary tensioning belt including fastening means for fastening the secondary tensioning belt around said primary support belt generally around the waist of the wearer to tension said back support belt, the improvements comprising, said secondary tensioning belt including readily visible back support belt tensioning indicator means distinct and remote from said secondary tensioning belt fastening means for indicating the tensioning of said back support belt, said back support belt tensioning indicator means being readily visible generally at the rear area of the waist of the wearer.

2. In a back support belt as in claim 1, the improvements further comprising, readily visible additional support belt tensioning indicator means operatively associated with said primary support belt fastening means and said secondary tensioning belt fastening means for further indicating the tensioning of said back support belt.

3. In a back support belt as in claim 1 wherein, said back support belt tensioning indicator means comprise color indicator means.

4. In a back support belt as in claim 2 wherein, said primary support belt fastening means and said secondary tensioning belt fastening means are operable to fasten said primary support belt and said secondary tensioning belt generally at the frontal area of the waist of the wearer, the improvements further comprising, said additional support belt tensioning indicator means comprising alignment means formed on said primary support belt fastening means for alignment therewith by said secondary tensioning belt fastening means, said alignment means being readily visible at the frontal area of the waist of the wearer.

5. In a back support belt as in claim 3 wherein, said color indicator means comprise a color indicator for indicating that the back support belt is not properly tensioned.

6. In a back support belt as in claim 3 wherein, said color indicator means comprise a color indicator for indicating that the back support belt is properly tensioned.

7. In a back support belt as in claim 3 wherein, said color indicator means comprise a color indicator of a color which readily contrasts with the color of said secondary tensioning belt for indicating that the back support belt is properly tensioned, and a color indicator of a different color which also readily contrasts with the color of said secondary tensioning belt for indicating that the back support belt is not properly tensioned.

8. In the back support belt as in claim 4 wherein, said alignment means comprise aligned, spaced alignment marks formed on said primary support belt for alignment of said secondary tensioning belt fastening means therewith.

9. In a back support belt as in claim 8 wherein, said alignment marks are colored in a color which readily contrasts with the color of said primary support belt fastening means.

10. In a method for indicating the tensioning of a back support belt which comprises a primary support belt including fastening means for fastening the primary support belt generally around the waist of the wearer, and a secondary tensioning belt including fastening means for fastening said secondary tensioning belt around said primary support belt generally around the waist of the wearer to tension said back support belt, the improvements comprising, the steps of, indicating the tensioning of said back support belt by providing readily visible back support belt tensioning indicator means on said secondary tensioning belt distinct and remote from said secondary belt fastening means, and disposing said back support belt tensioning indicator means on said secondary tensioning belt so that the same are readily visible generally at the rear area of the waist of the wearer.

11. In a method as in claim 10, the improvements further comprising, the steps of, further indicating the tensioning of said back support belt by providing readily visible additional support belt tensioning indicator means on said primary support belt fastening means for operative association with said secondary tensioning belt fastening means.

12. In a method as in claims 10 wherein, the provision of said back support belt tensioning indicator means comprises, the steps of, providing color indicator means to that effect.

13. In a method as in claim 11 wherein, said primary support belt fastening means and said secondary tensioning belt fastening means are operable to fasten said primary support belt and said secondary tensioning belt generally at the frontal area of the waist of the wearer, the provision of readily visible additional support belt tensioning indicator means on said primary support belt comprising, the steps of, forming alignment means on said primary support belt fastening means for alignment therewith by said secondary tensioning belt fastening means.

14. In a method as in claim 12 wherein, the provision of said color indicator means comprises, the steps of, providing a color indicator for indicating that said back support belt is not properly tensioned.

15. In a method as in claim 12 wherein, the provision of said color indicator means comprises, the steps of, providing a color indicator for indicating that said back support belt is properly tensioned.

16. In a method as in claim 12, wherein, the provision of said color indicator means comprises, the steps of, providing a color indictor of a color which readily contrasts with the color of said secondary tensioning belt for indicating that the back support belt is properly tensioned, and providing a color indicator of a different color which also readily contrasts with the color of said secondary tensioning belt for indicating that the back support belt is not properly tensioned.

17. In a method as in claim 13 wherein the formation of said alignment means on said primary support belt fastening means comprises, the steps of, forming spaced alignment marks on said primary support belt fastening means for alignment of said secondary tensioning belt fastening means therewith.

18. In a method as in claim 17 wherein the formation of said alignment marks comprises, the steps of, forming said alignment marks of a color which readily contrasts with that of said secondary tensioning belt.

\* \* \* \* \*